(12) United States Patent  
Gourlay (10) Patent No.: US 6,877,382 B1
(45) Date of Patent: Apr. 12, 2005

(54) INHALATION DETECTOR

(76) Inventor: Robert D Gourlay, 10400 Shirley Ave., Northridge, CA (US) 91326

( * ) Notice: Subject to any disclaimer, the term of this patent is extended or adjusted under 35 U.S.C. 154(b) by 23 days.

(21) Appl. No.: 10/689,214

(22) Filed: Oct. 20, 2003

(51) Int. Cl.[7] ............................................ G01P 15/125
(52) U.S. Cl. ...................... 73/718; 73/724; 73/514.32
(58) Field of Search ...................... 73/718, 724, 514.32

(56) References Cited

U.S. PATENT DOCUMENTS

| | | | |
|---|---|---|---|
| 4,366,716 A | * 1/1983 | Yoshida | 73/718 |
| 5,134,886 A | * 8/1992 | Ball | 73/718 |
| 5,531,128 A | * 7/1996 | Ryhanen | 73/862.623 |
| 5,641,911 A | * 6/1997 | Ryhanen | 73/718 |
| 6,496,348 B2 | * 12/2002 | McIntosh | 361/115 |
| 2001/0047689 A1 | * 12/2001 | McIntosh | 73/514.32 |
| 2002/0033048 A1 | * 3/2002 | McIntosh et al. | 73/514.32 |

* cited by examiner

Primary Examiner—Edward Lefkowitz
Assistant Examiner—Andr Allen (57) ABSTRACT

A detector providing an electrical signal in response to the pressures encountered in sensing breath inhalation in respirators. The detector uses a capacitive pressure sensor formed by a flexible conductive diaphragm separated from fixed electrodes by a layer of dielectric film. Deflection of the diaphragm by pressure introduces a low permittivity space in the sensor resulting in a substantial change in capacitance. The change in capacitance modifies the frequency of an oscillator. A frequency responsive circuit provides balancing electrostatic force feedback voltage to the diaphragm. The force feedback stiffens the diaphragm and maintains it in a high capacitance, high sensitivity state. This feedback reduces sensitivity to changes in the diaphragm mechanical properties. Signal filtering reduces the effects of long term drift and environmental factors.

7 Claims, 8 Drawing Sheets

INHALATION DETECTOR

CROSS-REFERENCE TO RELATED APPLICATIONS

Not Applicable

FEDERALLY SPONSORED RESEARCH

Not Applicable

SEQUENCE LISTING OR PROGRAM

Not Applicable

FIELD OF THE INVENTION

This invention relates to sensing the inhalation of breath in respirators and providing an electrical output to control the release of medication or gas in coordination with inhalation.

BACKGROUND OF THE INVENTION

The dispensing of medication via the respiratory system is receiving increasing use. Medications are commonly in the form of aerosols or powders obtained from pressurized containers or generated by atomizers. The dispensing methods used include patient operated hand-held respirators. To be effective the medication must be released in coordination with inhalation. Often the patient operates a control or actuator to release medication during inhalation.

In cases where coordinating the release of medication with inhalation is difficult or must be precisely controlled, an inhalation sensing mechanism is preferred to initiate the medication release. In U.S. Pat. No. 6,354,290 B1 Howlett describes a means to initiate the medication release with a vane that is deflected by the flow of the user's breath. Variations of this approach can be found in several patents. This type of respirator typically includes an arming or cocking control that the user manually activates to allow a subsequent inhalation to initiate the release of medication. The control is then manually reset for the next use. Consequently, this method is primarily used with medications that are administered in a single inhalation.

Extended Dosage

The dosage rate limit for drugs such as tobramycin (TOBI) is such that they must be applied over an extended period of breathing. Depending on the size and health of the patient, delivery of a dose will require 100 to 150 inhalations. Other drugs in either aerosol or powder form may deviate from this typical range. Manually activating the release of medication in coordination with inhalation for such a large number of steps is difficult for an active adult and virtually impossible for a pediatric or severely ill patient. The difficulty of this process is compounded if it is necessary to remove the respirator from the mouth or nose for each exhalation.

Respirator dispensation of drugs through extended breathing is substantially improved by automatically controlling medication release with an inhalation detector and permitting tidal breathing. That is, both inhale and exhale through the respirator. This seemingly simple change places an added set of requirements on the respirator. During a protracted breathing regimen a person with a serious lung ailment, a common user of such a device, has a very limited tolerance for resistance to air flow. Consequently, the air path through the respirator, including the inhalation detector, must have minimal pressure drop.

Tidal breathing and coughing may result in a backflow of moisture, medication, and sputum that coats internal respirator surfaces. Respirator elements that are exposed to this backflow must function with a coating of material that is often viscous, conductive, and corrosive. Because these backflow deposits can be highly infectious, the air passages, inhalation detector, and medication release device must either be disposable or regularly immersed in cleaning solutions. A typical cleaning process will consist of rinsing with agitated soapy water and/or a mild acid solution followed by flushing with running water. For cleaning processes to be effective the portion of the respirator exposed to contamination must be accessible to cleaning processes and free of crevices, holes, cavities, or absorbent surfaces.

Preferably, a dispensing respirator distributed through a pharmacy or medical practitioner for patient use will not require adjustment or calibration for or by the individual patient. The range of respiration flow rates such a respirator must accommodate is quite wide. The rate of a robust adult can be 10 to 12 times that of a child. Normal respiration flow rates fall between 7 and 80 liters per minute.

Requirements

The sensing of respiration is primarily a task of detecting the direction and magnitude of gas flow, usually air. The existing art of measuring gas flow has a long history and includes a wide range of processes. The task of sensing tidal respiration, particularly as applied to dispensing medication to the diseased or impaired, encounters several restrictions and demands that, in the aggregate, are not met by prior art.

The key requirements for an inhalation detector used in a tidal breathing respirator are:

(a) Operate at a pressure drop of no more than 0.04 cm $H_2O$ at a flow rate of 7 liters per minute.
(b) Function over a flow range of 7 to 80 liters per minute without adjustment.
(c) Tolerate abrupt surges such as encountered in coughing.
(d) Sense flow direction to discriminate between inhalation and exhalation.
(e) Properly operate after the backflow of moisture, sputum, and medication have coated mechanisms and surfaces.
(f) Tolerate regular flushing and cleaning with disinfectants.
(g) Configured to be free of crevices, cavities, or absorbent surfaces that may trap infectious residue.
(h) Operate at a power level suitable for battery operation.
(i) Have a low cost.

PRIOR ART

The primary task, the sensing of air flow, has been performed in prior art by a multitude of methods. Methods using lasers, ultrasonic sound, rotary vanes, and spark ionization have all been used for this purpose but are too large, complex, or costly for this application and will not receive further discussion.

Heated sensing devices that are cooled by air flow such as hot wires, thermistors, or heated films offer simplicity and moderate cost. An example is shown by Rusz et al in U.S. Pat. No. 5,094,246. To properly sense breathing, the thermal device must respond to a gentle air flow within a fraction of a second. To provide this rapid response the device must be very small with a low thermal conductivity mounting. Such sensors are usually fragile and vulnerable to the required cleaning processes. Further, the response time can be substantially slowed by a coating of backflow material. In addition, sensing the direction of flow with thermal devices requires significant complexity.

Vanes or flags that deflect with the movement of air offer both simplicity and directional sensitivity. At the low velocities to be sensed, the vane must be quite large to deliver enough force to operate a mechanical detector or switch. In U.S. Pat. No. 5,692,492 Bruna et al describe the inadequacies of sensing breath flow with mechanical devices. They note the disparity between the energy available from breath flow and that required to reliably operate mechanisms. Optical sensing of motion can allow the use of a small light-weight flag; however the vulnerability to cleaning damage and the effects of backflow deposits deter the use of the method in tidal breathing applications.

Pressure Sensing Methods

A very common form of flow sensor functions by detecting the pressure drop across an orifice, venturi, or other flow resistance. This pressure difference is converted to a suitable output, usually electrical, by a pressure transducer. Limiting the pressure drop through the sensor is a demanding requirement. A commonly accepted breathing resistance limit is 0.06 cm $H_2O$ of pressure for each liter per minute of air flow. This is based on a maximum flow rate of 80 liters per minute. The pressure drop through an orifice, venturi or similar restrictive path varies as the square of the flow velocity. Consequently, when a device is required to function at flow rates from 7 to 80 liters per minute, a range of roughly 11 to 1, the ratio of pressures to be sensed is 121 to 1. Using the aforementioned resistance limit, the pressure to be sensed with a pediatric patient can be expected to be as low as 0.04 cm $H_2O$ at 7 liters per minute.

The pressure sensors currently available in the commercial market have sensitivity ranges of 25 cm $H_2O$ or higher. An example is the General Electric NPC-1210 NovaSensor. The zero pressure output signals of these units can drift as much as 1% of full scale with respect to time and temperature; a variation of plus or minus 0.25 cm $H_2O$. When used to sense pressures as low as 0.04 cm $H_2O$, this error exceeds the value being sensed by a factor of six. Rubsamen et al in U.S. Pat. No. 5,450,336 and Ritson et al in U.S. Pat. No. 5,394,866 refer to this drift problem and describe a software means of correction. Their approach requires the added cost and complexity of a microprocessor and a stored look-up table that is custom tailored to each unit.

A pressure transducer concept to detect inhalation is described by Ball in U.S. Pat. No. 5,134,886. Ball does not address the drift errors discussed later by Rubsamen and Ritson. The Ball patent exemplifies the method commonly found in variable air-gap capacitive transducers. The transducer uses a thin (0.0013 cm) metallized plastic film diaphragm spaced from a fixed electrode as the preferred embodiment. Negative (inhalation) pressures draw the diaphragm toward the spaced electrode resulting in an increase in capacitance. This method has a low zero pressure capacitance and provides a small change in capacitance with respect to pressure. Because of the low capacitance it is vulnerable to noise, drift caused by external capacitance changes, and temperature effects. The flexibility of the plastic diaphragm can be degraded by deposits of backflow material, resulting in a loss of sensitivity. Measurements of transducer configurations similar to that of the Ball patent have shown a substantial zero pressure drift and a slow recovery from zero shifts following a surge in pressure. The configuration of the Ball embodiment cannot be cleaned without disassembly.

In U.S. Pat. No. 5,052,400, Dietz describes an inhalation detector similar to that of Ball. The primary difference from the Ball patent is the addition of an eductor. The stability of this design concept rests upon the physical properties of the diaphragm, the small capacitance change with pressure, and the vulnerability of the diaphragm to backflow deposits and deformation from pressure surges. The eductor has no effect on any of these factors and can be expected to provide no improvement in the drift deficiencies of this configuration. The Dietz embodiment requires disassembly to clean and uses a configuration unsuited for integration into a hand-held respirator.

Objects and Advantages

The primary purpose of the inhalation detector is to sense the inhalation phase of breathing through a respirator and provide an electrical output to control the release of gas or medication in coordination with the inhalation.

(a) An object of the inhalation detector is to sense inhalation over a wide range of flow rates while presenting a low resistance to breathing. This combination of flow rates and low resistance requires the capability to sense pressures as low as 0.04 cm $H_2O$ with stability. The operation of prior art sensors at such low pressures results in excessive error and drift.

(b) Another object is to provide the required inhalation detector performance after exposure to a backflow of moisture, medication, and sputum. A coating of these materials on the thin pressure sensing diaphragms used in prior art degrades the response to pressure.

(c) Another object is to tolerate flow surges caused by coughing and gasping. In prior art sensors, the thin plastic diaphragms needed to achieve the necessary sensitivity can be stressed by such surges resulting in an output offset. Such an offset provides an erroneous response.

(d) Another object is to avoid surfaces or configurations that provide sites for infectious deposits. Prior art contains cavities, small tabulations, and ports that create difficult to clean traps for deposits.

(e) Another object is to tolerate cleaning processes. Prior art sensors either have sensitive elements that will be damaged by the forces of cleaning or do not provide a path for cleaning fluids to access all elements subject to contamination.

(f) Another object is to fit the detector within the confines of a hand-held respirator. Prior art devices with sufficient sensitivity for use in a respirator require a sensing device size or configuration unsuited for hand-held use.

Additional objects and advantages will become evident from a review of the following description and drawings.

SUMMARY OF THE INVENTION

The invention is a device for generating an electrical output in response to an inhalation of breath through a respirator. A primary application is controlling the release of medication or gas in coordination with inhalation. The device uses a sensitive sensing method, feedback, and electrical filtering techniques to obtain the stability and sensitivity needed for detecting the low breath flow rates encountered with pediatric and disabled patients. The feedback technique provides a tolerance for deposits of sputum and medication residue in the detector.

DRAWINGS—Figures

In the drawings.

DRAWINGS—Reference Numerals

| | DRAWINGS - Reference Numerals |
|---|---|
| 12 | Electrodes. |
| 13 | Conductive vias through the base. |
| 14 | Insulating coating. |
| 15 | Conductive adhesive. |
| 16 | Metallic coating on the pressure diaphragm. |
| 17 | Pressure diaphragm. |
| 18 | Vent hole in the insulating coating. |
| 19 | Pressure sensor base insulator. |
| 20 | Pressure sensor base assembly. |
| 21 | Contact pads. |
| 22 | Vent hole through the base. |
| 30 | Pressure sensor assembly. |
| 31 | Oscillator circuit. |
| 33 | One-shot circuit. |
| 34 | Integrator output signal. |
| 52 | Inhaler flow restriction. |
| 53 | Spring contact. |
| 54 | Adhesive sealant. |
| 56 | Detection electronics module. |
| 58 | Inhaler housing. |
| 60 | Alternate embodiment sensor base assembly. |
| 62 | Alternate embodiment base insulator. |
| 64 | Alternate embodiment connection clip |
| 66 | Alternate embodiment contact area. |
| 67 | Adhesive |
| C1 | Integration capacitor. |
| C2 | Boost filter capacitor. |
| C3 | Low pass filter capacitor. |
| C4 | Differentiating capacitor. |
| C5 | Timing Capacitor. |
| D1 | Secondary feedback coupling diode. |
| D2 | Turn-off enhancement diode. |
| D3 | Boost rectifier. |
| D4 | Trigger coupling diode. |
| IC1 | Dual Operational amplifier |
| IC2 | Comparator |
| IC3 | Quad NOR Gate |
| L1 | Boost inductor. |
| Q1 | Secondary feedback transistor. |
| Q2 | Primary feedback transistor. |
| Q3 | Boost transistor. |
| R1 | Isolation resistor. |
| R2 | Integration resistor. |
| R3 | Filter resistor |
| R4 | Offset resistor. |

-continued

| | DRAWINGS - Reference Numerals |
|---|---|
| R5 | Hysteresis resistor. |
| R6 | Limiting resistor. |
| R7 | Load resistor. |
| R8 | Timing resistor. |
| R9 | Load resistor. |
| R10 | Differentiating resistor. |
| R11 | Timing resistor. |
| Vo | Output voltage |
| V+ | Supply voltage |
| HV+ | Boosted voltage |

DETAILED DESCRIPTION

Preferred Embodiment

The inhalation detector is comprised of two major elements, a pressure sensor and detection electronics.

Pressure Sensor

Sensing Method

The pressure sensor provides a change in capacitance in response to a change in pressure across a sensing diaphragm. An electrically conductive pressure responsive diaphragm is located in close proximity to a planar pair of fixed sensing electrodes. At zero pressure the distance between the conductive diaphragm and the fixed sensing electrodes is determined by a thin insulator. The insulator provides firm control of this distance while allowing minimum thickness. The close spacing and the higher dielectric constant (permittivity) of the insulator provides a significantly higher capacitance than obtainable in an air-gap sensor. Deflection of the diaphragm by pressure introduces a space that not only increases the distance between the diaphragm and the sensing electrodes; it significantly reduces the dielectric constant of the sensor capacitance. The result is a substantially larger change of capacitance than an increase in spacing alone can bring. This variable dielectric characteristic distinguishes the sensor from the variable air-gap and variable area types. The close proximity of the diaphragm to the sensing electrodes limits the diaphragm deflection to a single direction, away from the sensing electrodes.

Sensor Elements

Figure 1:
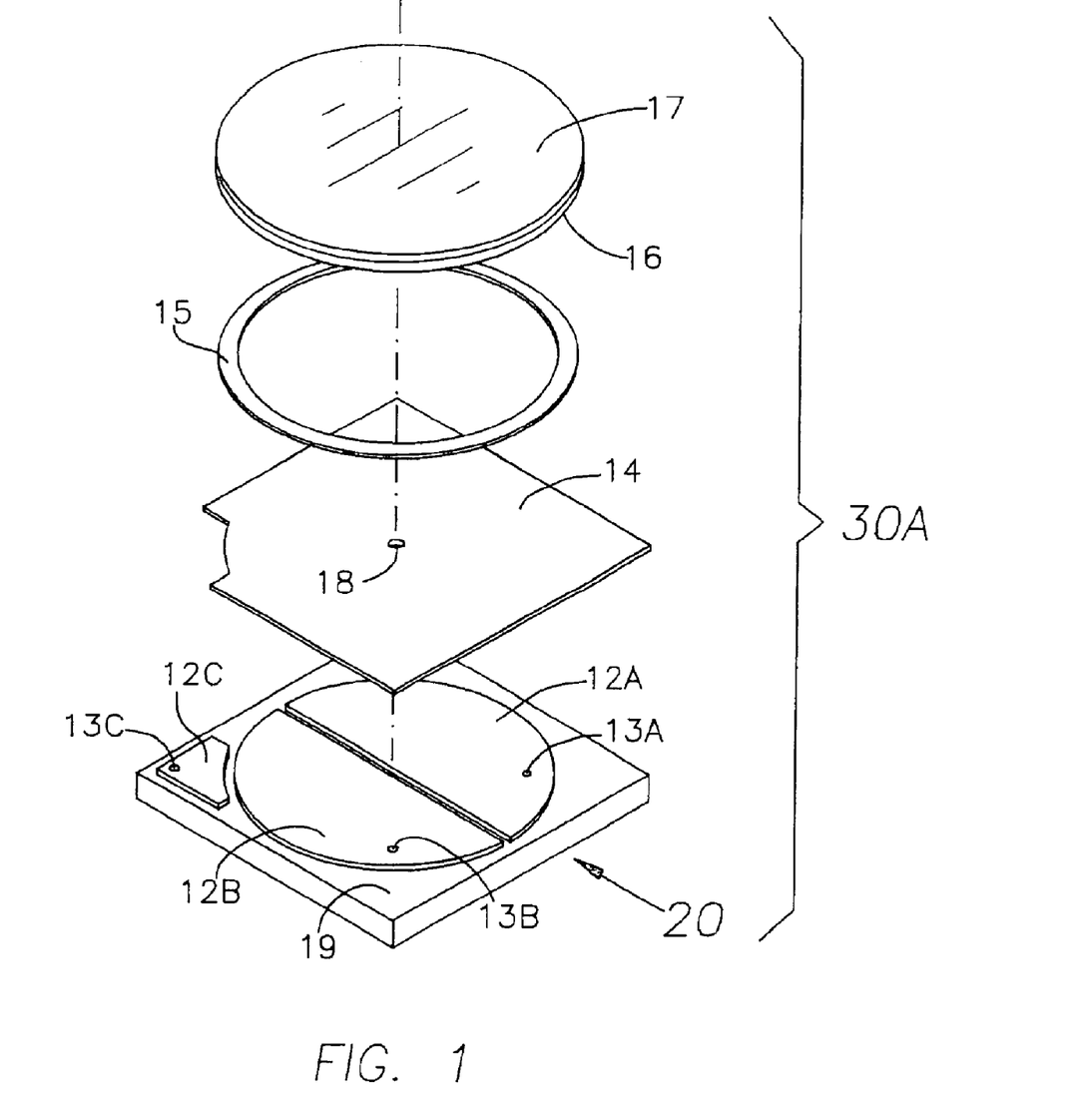
FIG. 1 is an exploded view of the pressure sensor showing the relationship between the base assembly, the insulating coating, the adhesive, and the pressure diaphragm.

The primary components of pressure sensor 30A are shown in FIG. 1. A base structure, item 20, provides support for the remaining elements of the sensor. Base 20 is similar to the etched copper printed wiring boards (PWB) widely used in electronic equipment. A pair of semi-circular sensing electrodes 12A and 12B is etched from the copper surface of the insulating board forming the base. A third smaller electrode 12C is located in the corner of the base. Two features commonly provided in PWB construction are used in the base design. These features are electrically conductive paths connecting the copper on opposite faces of the base and an insulating coating over the base surface. The conducting paths are commonly referred to as vias or plated through holes. These are holes through a base insulator 19 that are lined with a cylindrical layer of metal conductor. A set of three vias 13A, 13B and 13C are used. An insulating coating 14, commonly described as solder mask, is applied by a photo-lithographic process to cover selected portions of the upper surface of the base. A diaphragm 17 with a metallized coating 16 is bonded to the insulating coating with a ring of adhesive 15.

Sensor Design

Figure 2:
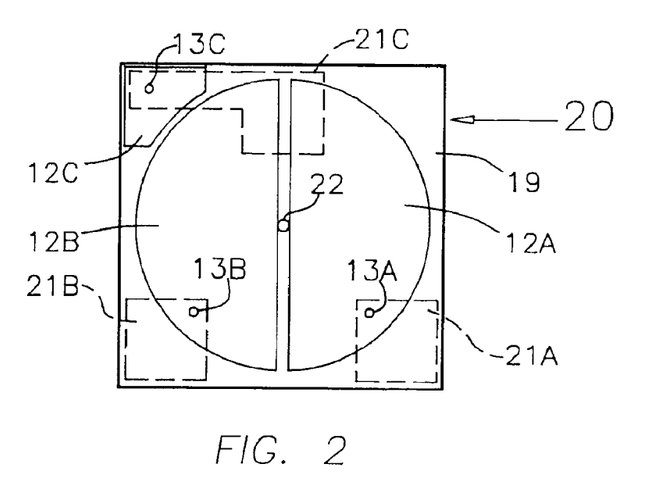
FIG. 2 is a plan view of the pressure sensor base assembly showing the locations of the sensing electrodes and the contact areas on the reverse side.

As shown in FIG. 2, a copper layer on the bottom face of the base is etched to form a set of contact pads 21A, 21B, and 21C. Base insulator 19 is nominally 0.127 cm (0.05 inch) thick and made from an epoxy impregnated glass fiber laminate. A vent hole 22 through the base insulator is located in the center. Sensing electrodes 12A and 12B are segments of a 1.9 cm (0.75 inch) diameter circle. Contact pads 21A, 21B, and 21C are 0.43 cm (0.17 inch) square. The copper layers are 0.0036 cm (0.0014 inch) thick. The sensing electrodes and contact pads are connected by vias 13A, 13B, and 13C. The vias are 0.036 cm (0.014 inch) in diameter. The contact pads serve as connection points to the associated detection electronics. The values for the thickness of the copper coating, the dimensions of the vias and contact pads, and the thickness of the base represent convenient choices used in tests. Substantial deviation from these values has little effect on the performance of the sensor.

Figure 5:
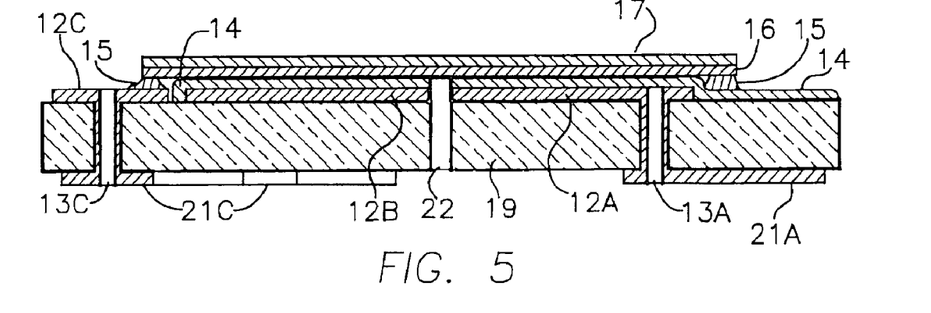
FIG. 5 is a section view of the pressure sensor showing the connection paths between the electrodes and contact areas provided by the vias.

As shown in FIGS. 1 and 5, the pressure sensitive element of the sensor is diaphragm 17 with metal film coating 16 on the bottom face. This diaphragm is approximately 0.00091 cm (0.00036 inch) thick plastic film with a 0.00001 cm (0.000004 inch) metal coating. The metal coating is aluminum. Coated films of this type are readily available commercially and commonly used to fabricate capacitors. Polycarbonate and polyvinyledine fluoride (PVDF) films have proven satisfactory.

Insulating coating 14 in FIGS. 1 and 5 provides a layer of insulation between sensing electrodes 12A and 12B and diaphragm metallization 16. The coating is shaped to provide a small central vent hole 18 in alignment with vent hole 22. A gap in the corner of the coating provides a connection path between metallization 16 and electrode 12C. The insulating coating is 0.002 cm (0.0008 inch) thick. The diaphragm is attached to the insulating coating by adhesive 15. The adhesive performs an additional function; it provides an electrical connection between metal film 16 and electrode 12C through the gap in the insulating coating. The adhesive is made electrically conductive by an additive. A common additive for this purpose is silver powder. In this usage the electrical currents through the adhesive are very small. Consequently, low cost alternate additives such as carbon or graphite powders are also suitable. A variety of conductive adhesives are commercially available.

Figure 4:
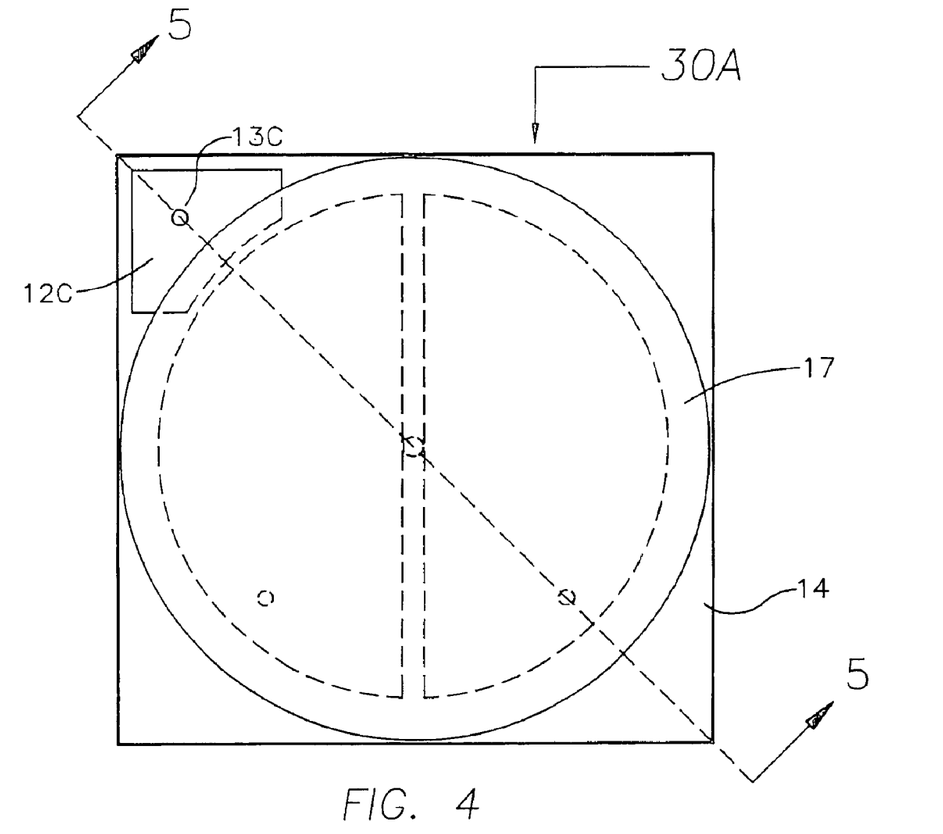
FIG. 4 is a plan view of the pressure sensor showing the cut line of the FIG. 5 section view.

FIG. 4 shows a plan view of sensor 30A and the cut line for section view FIG. 5. FIG. 5 displays the sensor configuration as assembled. The interrelationship between electrodes 12, contact pads 21, and vias 13 is shown. The thickness of some elements has been substantially exaggerated for clarity.

Alternative Embodiment

This alternative applies to the pressure sensor only, the detection electronics are unaffected. The operating principles and the function of the sensor are unchanged. The primary variation from the preferred embodiment is the inversion of the pressure sensing diaphragm. That is, the metallized surface rather than the plastic film is exposed to the airflow being sensed. Consequently, the insulating coating on the sensor base and the conductive additive in the adhesive are eliminated. A connection clip is added to provide a signal path to the diaphragm metallization.

Figure 8:
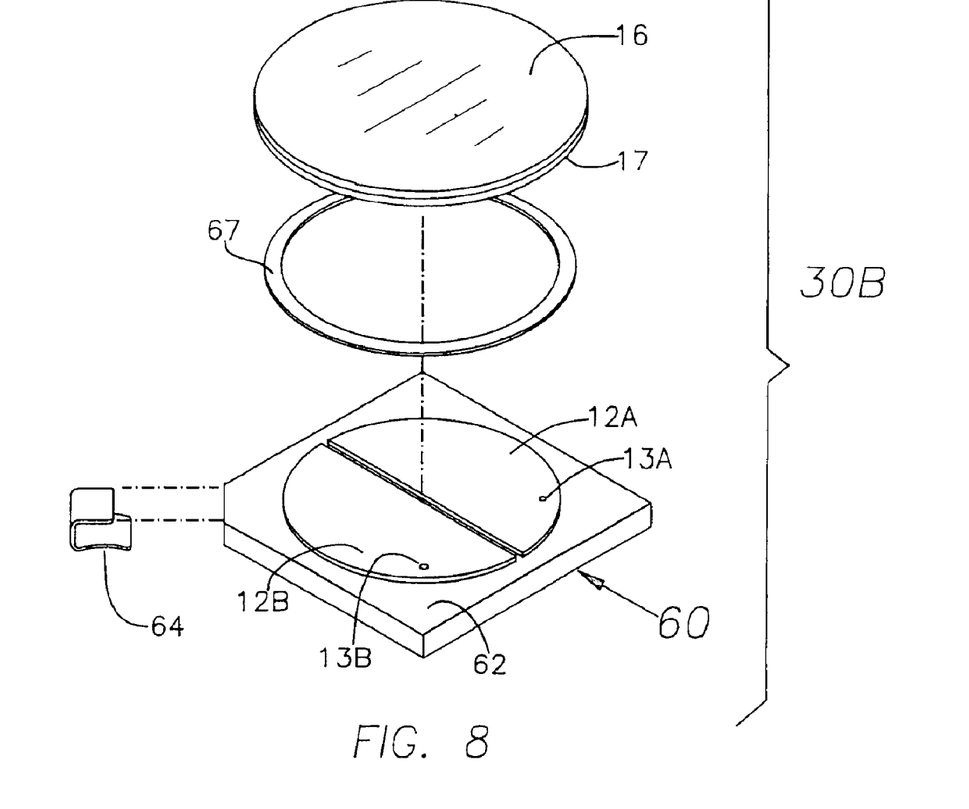
FIG. 8 is an exploded view of the alternate embodiment of the pressure sensor showing the alternate method of connecting the diaphragm metal to the contact area on the base.

FIG. 8 is an exploded view of the alternative sensor configuration, 30B. A sensor base 60 consists of a base insulator 62 with etched sensing electrodes 12A and 12B and with vias 13A and 13B providing an electrical path through the base insulator. The corner of the base insulator is beveled to accept a conductive connection clip 64. Diaphragm 17 is bonded to the base around the periphery of the electrodes with a ring of adhesive 67. The adhesive does not contain a conductive additive. The connection clip is installed following the bonding process.

Figure 9:
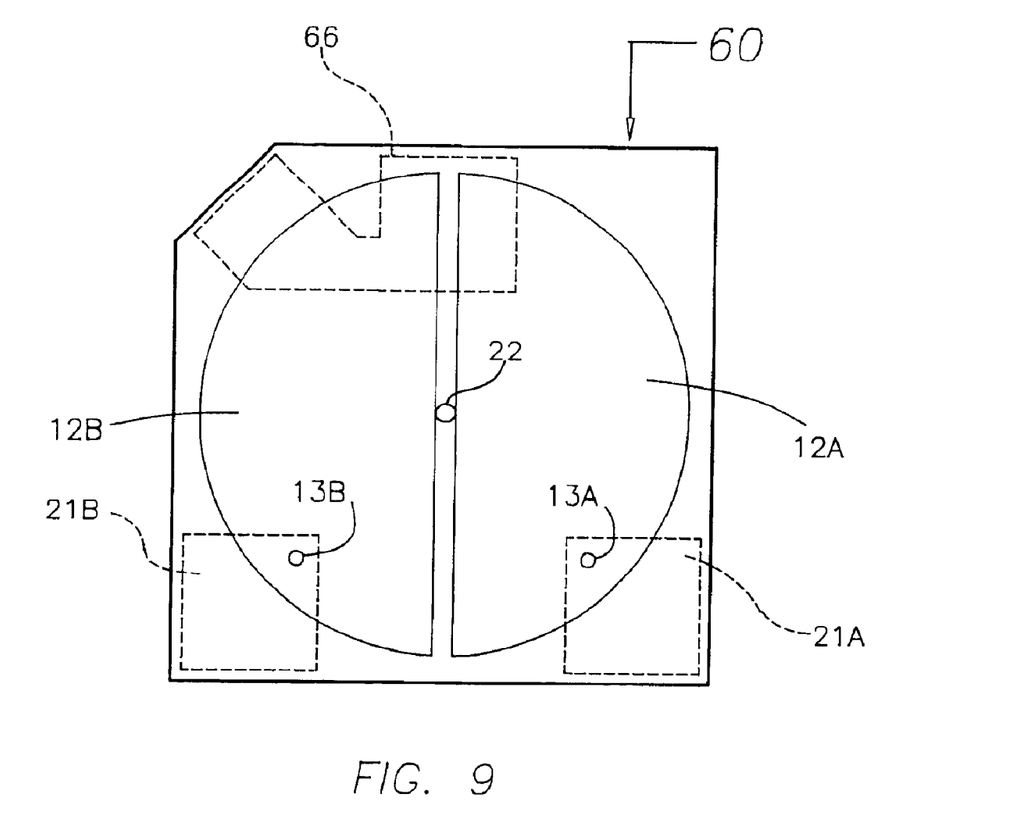
FIG. 9 is a plan view of the circuit board of the alternate embodiment showing modified configuration of the contact metal area.

FIG. 9 shows a plan view of base 60. In addition to the electrodes, the positions of contact pads 21A and 21B etched on the bottom side of the base are shown. Also shown is a contact pad 66 shaped to provide contact with the connection clip. Vent hole 22 is positioned in the center of the base.

Figure 10:
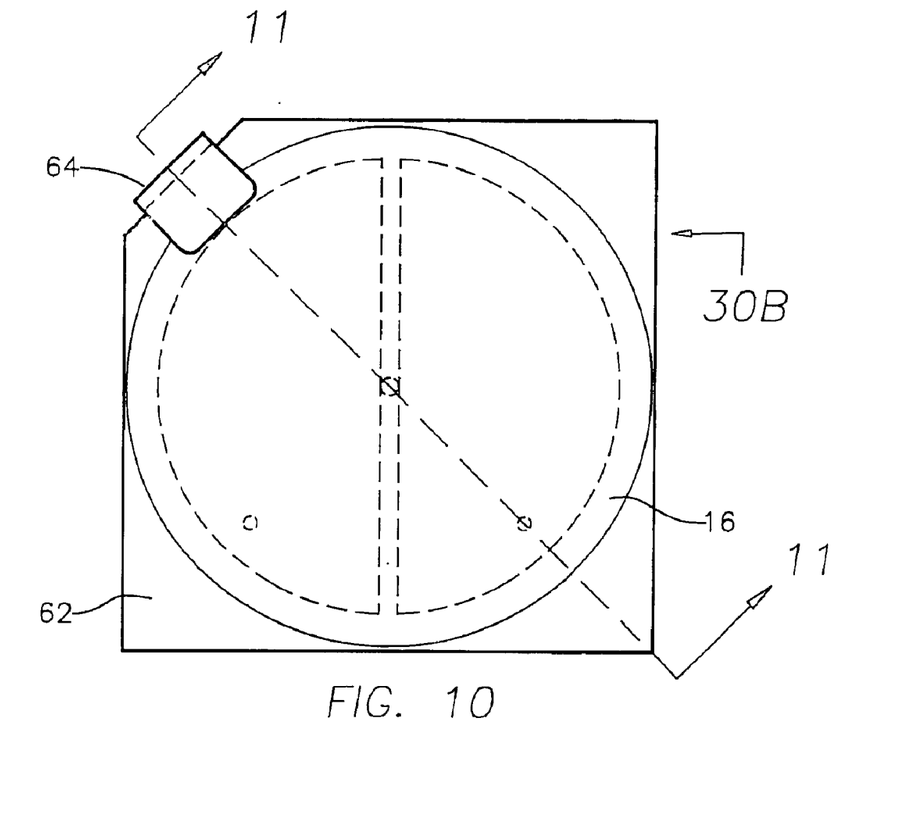
FIG. 10 is a plan view of the alternate embodiment of the pressure sensor showing the locations of the connection clip and the section cut line.
Figure 11:
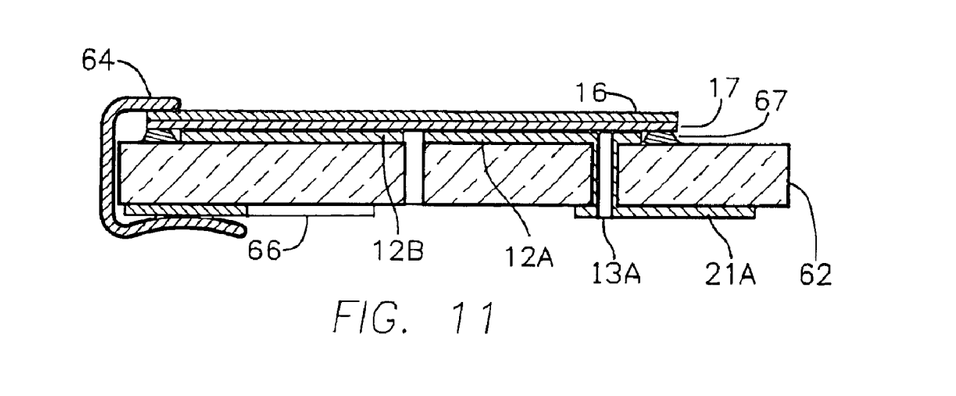
FIG. 11 is a section view of the alternate embodiment of the pressure sensor.

FIG. 10 is a plan view of pressure sensor 30B showing the positioning of the connection clip and the cut line for cross section view FIG. 11. Section view FIG. 11 shows the signal path from diaphragm metallization 16 through the connection clip to contact pad 66. The position of the adhesive bonding the diaphragm to the base insulator is also shown. The thickness of some elements has been substantially exaggerated for clarity.

Operation

Pressure Sensor—FIG. 1

Semicircular sensing electrodes 12A and 12B each function as one plate of two separate capacitors. A common opposing plate for these capacitors is provided by metal film 16 on the face of diaphragm 17. The upper surface of the diaphragm is exposed to the pressure being sensed. The reference pressure, typically the local ambient pressure, reaches the lower side of the diaphragm through holes 18 and 22 (FIG. 5). When sensed at contact pads 21A and 21B (FIG. 2) the two capacitors are electrically in series. As diaphragm 17 is deflected by pressure, the change in spacing between metal film 16 and sensing electrodes 12A and 12B causes a change in capacitance detectable at contact pads 21A and 21B. The associated detection electronics converts this capacitance change to an output voltage.

The detection electronics also apply electrostatic force feedback to control diaphragm deflection. The electrostatic force is created by applying a DC voltage between the diaphragm metallization 16 and sensing electrodes 12A and 12B. The sensitivity of the sensor is primarily controlled by the electrostatic feedback. The sensor output is highly amplified and applied as an opposing electrostatic force to the diaphragm. The diaphragm is thereby maintained in a high capacitance force balanced state. Pressure tending to deflect the diaphragm is opposed by electrostatic attraction between the diaphragm metallization and the sensing electrodes. The gain of the feedback system is sufficient to keep the diaphragm virtually motionless with applied pressure. With diaphragm deflection reduced to a negligible value, the mechanical properties of the diaphragm have only a minor effect on the sensitivity of the sensor. The effects of changes in diaphragm properties due to manufacturing variations, aging, temperature, and backflow deposits are substantially reduced. The magnitude of the feedback voltage is used as the measure of pressure.

Detection Electronics

Circuit Functions

Figure 6:
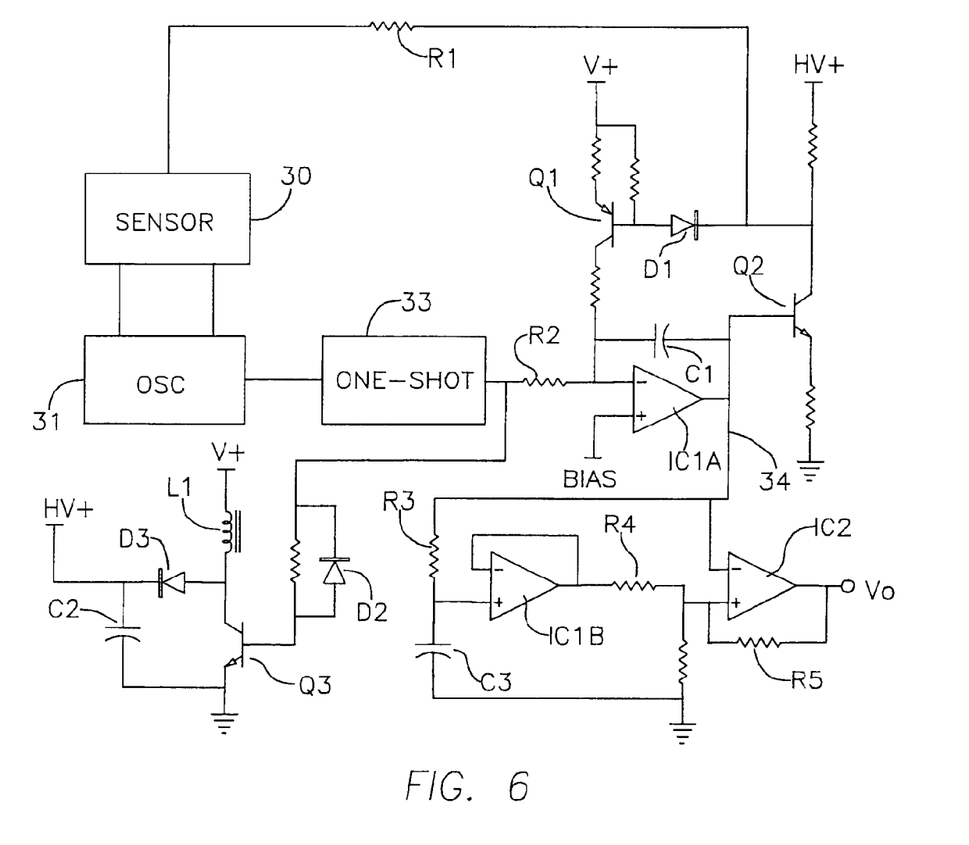
FIG. 6 is a detection electronics schematic. The sensor, oscillator, and one-shot are shown as blocks that are detailed separately.

The conversion and amplifying circuits of FIG. 6 convert a specific capacitance change of the pressure sensor into a change in voltage. That voltage is amplified and compared to a reference voltage. If the voltage exceeds the reference level it triggers a logic level change at output Vo. The circuit also provides electrostatic force feedback to the sensor and time selective filtering to reduce the effects of circuit and sensor drift. A voltage boost function is included to power the electrostatic feedback when operating from low voltage batteries. The unlabeled parts in FIG. 6 have functions that are evident to those skilled in the art and require no further detail. An oscillator 31, a one-shot (monostable multivibrator) 33, and a sensor 30 are shown as blocks in FIG. 6; however they are shown in detail in FIG. 7. Sensor variations 30A and 30B are electrically equivalent and designated sensor 30 in FIGS. 6 and 7.

Circuit Configuration

Oscillator 31 generates a rectangular waveform that varies in frequency in response to the capacitance presented by pressure sensor 30. This waveform triggers a constant width pulse from one-shot 33 in response to each cycle of the oscillator waveform. This train of constant width, variable frequency pulses is fed to an integrator formed by a resistor R2, a capacitor C1 and an operational amplifier (opamp) IC1A. An integrator output 34 is connected to three places, a transistor Q2, a comparator IC2, and a resistor R3. Transistor Q2 amplifies the integrator output to provide electrostatic force feedback to pressure sensor 30 through a resistor R1. The integrator output is also applied to the inverting (negative) input of the comparator. The third use of the integrator output is to drive a low-pass filter stage consisting of resistor R3, a capacitor C3 and a unity gain buffer amplifier IC1B. The buffer output supplies a bias level to the non-inverting (positive) input of comparator IC2 through a resistor R4. A resistor R5 provides positive feedback around the comparator. A comparator output Vo provides logic level output signals indicating inhalation is taking place. The output of one-shot 33 also drives the voltage boost circuit that supplies an output HV+. The boost circuit consists of a transistor Q3, an inductor L1, a capacitor C2, and a pair of diodes D2 and D3. A transistor Q1 and a diode D1 provide a secondary feedback path around the integrator.

To avoid the need for a negative power source, the non-inverting (positive) input of the integrator opamp is connected to BIAS voltage to place its nominal output 1.5V above power return (ground). A voltage bus V+ is supplied by an external battery or source, not shown. To simplify the drawings, the connections between bus V+ and integrated circuits IC1, IC2, and IC3 are not shown. The supply voltage range for the preferred embodiment is 4.0 to 6.0 volts dc. With a few value changes those skilled in the art can adjust the circuit for different supply voltages.

Circuit Components

The perform ance requirements for the opamp are not demanding; several commercially available devices will suffice. The National Semiconductor LM324 provides the necessary properties. The National Semiconductor LM339 is suitable for the comparator function. The function of transistors Q2 and Q3 can be performed with type 2N5551 devices and that of transistor Q1 by type 2N5087. Requirements for diode D2 can be met by a type 1N4148. Diodes D1 and D3 require a higher voltage rating, type BAS21 is suitable.

Figure 7:
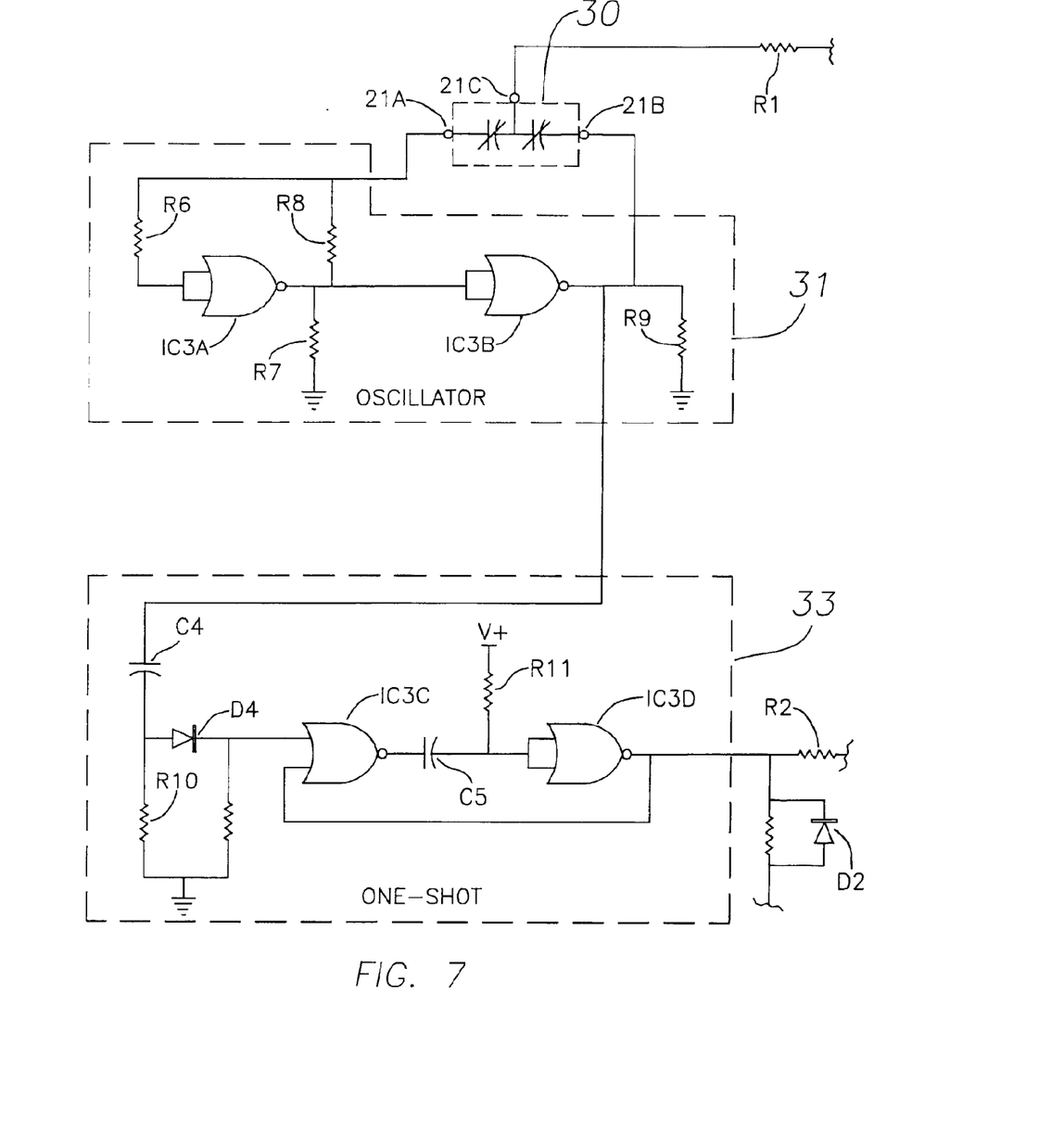
FIG. 7 is a schematic of the circuit details of the oscillator, one-shot, and sensor elements of the detection electronics.

As shown in FIG. 7, oscillator 31 is formed with a pair of complementary metal oxide semiconductor (CMOS) logic gates IC3A and IC3B. These devices are part of a 74HC02 QUAD NOR gate. This type of oscillator using CMOS logic gates is widely used and common in the art. Design details can be found in application notes provided by logic gate manufacturers. Both Motorola and National Semiconductor provide such notes. A pair of resistors R7 and R9 provides a path to ground for both terminals of pressure sensor 30. A resistor R6 limits the loading of IC3A on the timing elements. The frequency of the oscillator is determined by the value of a resistor R8 and the capacitance presented between contact pads 21A and 21B by pressure sensor 30. Gates IC3C and IC3D used in one-shot 33 are the same type of CMOS gate used in the oscillator. This circuit is also commonly used in the art. A capacitor C4 couples the output of the oscillator to trigger the one-shot. For the one-shot to function properly, the input trigger must end before completion of the one-shot output pulse. The values of capacitor C4 and a resistor R10 are chosen to differentiate the oscillator output into short positive and negative pulses to meet this requirement. A diode D4 selects the positive pulses to trigger the one-shot. The time duration of the one-shot output pulse is set by the values of a capacitor C5 and a resistor R11.

Operation

Detection Electronics—FIG. 6

The time constants in the detection electronics are selected with consideration of the timing of the human respiration cycle. The primary purpose of the invention is to sense the duration of the inhalation period during tidal breathing. On average this period is one second. It can vary from one-half this value in children to twice the value in some adults. The frequency of oscillator 31 is chosen to be much higher than the respiration cycle. The frequency selected is 13 KHz. The pulse width of one-shot 33 is nominally 25 microseconds. The integrator time constant, defined by the product of resistor R2 and capacitor C1, is 0.20 seconds. This time constant allows the integrator output to follow the respiration cycle yet filter the oscillator frequency components from the output. This time constant also reduces the effect of abrupt transients resulting from gasping or coughing.

When no pressure change is applied to the sensor, the integrator output is nominally 1.5V. A pressure reduction at the sensor resulting from inhalation causes the oscillator frequency to increase with a resulting increase in duty cycle at the output of the one-shot. This increase in duty cycle provides a higher average voltage at the integrator input. The integrator is an inverting amplifier that delivers an output proportional to the inverse of the average voltage input. Consequently, an inhalation causes a reduction in voltage at the inverting (negative) input to comparator IC2.

When this input falls below the bias potential at the non-inverting (positive) input of the comparator, output Vo transfers from a low to a high logic state thereby indicating an inhalation. The comparator only responds to differences between the two inputs and ignores changes common to both inputs.

Filter, FIG. 6

The non-inverting input bias to the comparator is obtained from a filtered version of the same integrator output 34 applied to the inverting input. The low-pass filter provided by resistor R3 and capacitor C3 has a time constant of 10 seconds, appreciably longer than a respiration cycle. The resulting performance allows slow changes due to temperature, sensor drift, and battery decay th at occur over time periods considerably longer than 10 seconds to appear at both comparator inputs and cancel. More rapid changes resulting from respiration are substantially reduced by the low-pass filter to minimize the cancellation effect. Unity gain buffer IC1B prevents loading of the low-pass filter by the comparator circuit thereby allowing the use of smaller components in the filter. Resistor R3 has a value of 4.7 megohms and capacitor C3 has a value of 2.2 microfarads. Resistor R4 provides a voltage drop of 25 millivolts between the buffer output and the comparator input. This voltage difference establishes a threshold level for sensing changes in the integrator output. Resistor R5 provides positive feedback to the comparator to create hysteresis that reduces the sensitivity to noise. This use of hysteresis with comparators is a common practice well known to those skilled in the art. This addition of hysteresis increases the comparator threshold from 25 to 50 millivolts.

Feedback, FIG. 6

Output signal 34 from integrator opamp IC1A is amplified by transistor Q2 and applied to the sensor as electrostatic negative feedback. The reduction in integrator output voltage resulting from inhalation is inverted by transistor Q2 to increase the voltage between the diaphragm metallization and the sensing electrodes in the sensor. This voltage change increases the electrostatic force on the diaphragm to oppose the pressure difference caused by inhalation. Because the voltage gain of the integrator is in excess of 100,000, this negative feedback limits the diaphragm motion resulting from pressure change to a negligibly small value. Resistor R1 is chosen to be much larger than resistors R7, R8 and R9 in FIG. 7 to assure that feedback voltage applied to the sensor will not improperly affect oscillator performance. The value of resistor R1 is 4.7 megohms.

Voltage Boost, FIG. 6

The voltage needed to electrostatically balance the sensor exceeds that normally available from the batteries in a respirator. A voltage increase is obtained with a circuit commonly known in the art as a flyback converter. In this circuit transistor Q3 is switched from the off to the on state by the fixed width positive pulses from the one-shot (33). During this on-time, essentially all the V+ voltage from the power source is imposed across inductor L1. Current through the inductor rises linearly during the on-time, storing energy in the inductor. As the one-shot voltage subsequently transfers to the low state, the current through the collector of transistor Q3 ceases and the magnetic field in the inductor begins to collapse. This field collapse causes a substantial change in voltage across the inductor that boosts the voltage at the transistor collector well above V+. The amount of boost is affected by the rapidity of the inductor current turn-off. Diode D2 speeds up the turn-off process. The collector voltage rise charges capacitor C2 through diode D3 to supply boosted collector voltage HV+ for transistor Q2. During the off-time of transistor Q3, energy in the inductor is transferred to capacitor C2 and remains quiescent until the next high state pulse from the one-shot. The value of inductor L1 is established by the energy required by the negative feedback circuit and the pulse width and frequency of the one-shot. The value used is 10 millihenry. The value of capacitor C2 is 0.0047 microfarad. When V+ is 5V, the dc voltage on HV+ is 70V.

Exhalation Effects, FIG. 6

Electrostatic feedback can only apply attractive force to the sensor diaphragm; therefore it can only balance negative (inhalation) pressures. Diaphragm motion from positive (exhalation) pressures is mechanically limited by the proximity of the diaphragm to the sensing electrodes but lacking in feedback control. During positive pressures the integrator operates without feedback and, unless controlled, the output voltage will rise toward opamp IC1A's upper limit. The resulting voltage charge on integration capacitor C1, delays the recovery of the integrator during the following inhalation cycle. To remedy this effect, an secondary feedback path that functions during exhalation pressures is provided through transistor Q1. During inhalation periods the feedback voltage at the collector of transistor Q2 exceeds V+ and diode D1 is reverse biased. Consequently transistor Q1 is cut-off and delivers no current to the input of integrator opamp IC1A. Transistor Q1 is chosen to be a low leakage device to avoid adverse effect on the integrator. A type 2N5087 is suitable. A rising voltage at the integrator output due to loss of feedback causes the collector of transistor Q2 to fall, thereby causing diode D1 to conduct and activate transistor Q1. This event closes a secondary feedback path around the integrator to keep the integrator in a stable, rapid recovery state until the next inhalation.

Figure 3:
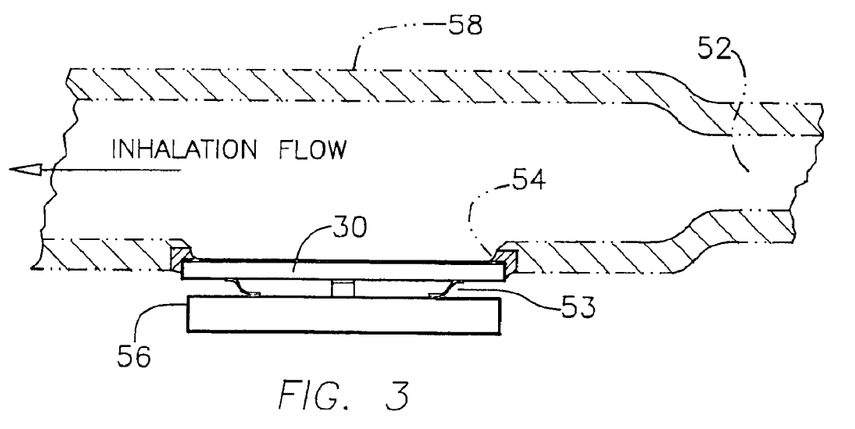
FIG. 3 illustrates a typical mounting of the inhalation detector to a respirator flow path. The respirator is shown in section view.

Typical Application—FIG. 3

FIG. 3 shows an example of applying the inhalation sensor to the airway of a typical respirator. The respirator is represented by a housing 58 and a flow restriction or orifice 52. Pressure sensor 30 is bonded into the housing with an adhesive and sealant 54. The sensor diaphragm is exposed to the interior of the housing. A detection electronics module 56 is fitted with a set of spring contacts 53 to make electrical connection with the pressure sensor. This arrangement allows for separation of the pressure sensor from the detection electronics if the airway is disposable or needs to be separated for cleaning. Assembly of the detection electronics in a configuration similar to module 56 is readily performed by those skilled in the art and is not described. When the detector is installed in this fashion, only the diaphragm surface and a fillet of adhesive are exposed to the airway. Consequently traps for infectious deposits are minimized and cleaning is simplified. The sensing electrodes supporting the diaphragm protect against damaging deflections from pressure surges and cleaning processes.

Conclusion

The inhalation detector provides the control function needed for coordinated dispensing of medication or gases into the respiratory system. It provides this function for a wide range of patient respiratory capabilities and where tidal breathing is necessary. Variable dielectric operation of the pressure sensor results in sensitivity and stability improvements over prior art variable gap sensors. The use of electrostatic force feedback reduces errors and drift caused by variations in sensing diaphragm properties and the effects of moisture, medication, and sputum deposits. Signal filtering reduces slow drift errors caused by aging, temperature, and power source changes. These stabilization methods provide the sensitivity and low drift rate needed to serve pediatric and breathing impaired patients. Maintaining the sensing diaphragm in close proximity to the supporting sensing electrodes protects against the rigors of cleaning procedures and surges caused by coughing. The capability for flush placement in the wall of a respirator airway allows a smooth surface free of infectious residue traps and permits simplified cleaning procedures. The physical size and power consumption are suited for use in hand-held respirators needed for self-administered care.

Variations

The descriptions in the embodiments are specific in detail to assure those reasonably skilled in the art can successfully make and use the invention. Several variations of that detail will also yield the claimed performance.

(a) Electrodes 12 may be formed in a variety of geometric shapes other than semi-circular. Included shapes are rectangular and concentric configurations.

(b) The electrodes need not be etched from a copper coated insulator. They can be bonded, plated, printed, or painted on an insulator with a conductive material.

(c) The size or area of the sensing electrodes and diaphragm can differ substantially from the embodiment. The limits are the available space in the particular application and the impact on sensitivity.

(d) The diaphragm need not be adhesive bonded in place. Thermal welding and clamping processes are alternatives. Laminated plastic films that can facilitate thermal welding while retaining desirable electrical and mechanical properties of the film are available.
(e) The diaphragm can be other than metallized plastic film. It can be formed of metal alone or a lamination of electrical conductor and an insulator.
(f) The detection electronics need not be configured as a separate assembly. They can be placed on the face of the base insulator opposite the electrodes.
(g) The time constants used in the detection electronics are based on nominal human respiration values and convenient choices of circuit components. Considerable deviation in timing is allowable while retaining the functions of the inhalation detector.
(h) The electronic components used in the detection electronics were selected from the large array of devices currently available. Those skilled in the art will be able to select and substitute alternate components with similar functions without.
(i) changing the essential detection processes.
(j) In addition to a direct connection, the detector output Vo can be coupled to the controlled device via an optical, audio, or radio wave path.
(k) Because the hand-held respirator presents the most demanding requirements for an inhalation detector, the embodiments described have emphasized this application. The invention is equally suited for other forms of respiratory care or monitoring.

Scope

The embodiments and variations described herein are intended to be exemplary and should not be construed as limiting the scope of the appended claims or their legal equivalents.

What is claimed is:

1. A detector providing an electrical signal in response to a predetermined pressure difference comprised of:
    a. a diaphragm responsive to said predetermined pressure difference and a pair of electrodes, fixed in planar form, cooperating with and facing said diaphragm;
    b. an insulator sandwiched between and contiguous with said diaphragm and said electrodes;
    c. an oscillator having a frequency responsive to a capacitance between said electrodes, a monostable multivibrator responsive to said oscillator, and an integrator averaging a waveform from said monostable multivibrator to provide a feedback voltage;
    d. a feedback means applying said feedback voltage across said diaphragm and said electrodes whereby electrostatic forces upon said diaphragm maintain said capacitance substantially constant;
    e. a comparator means providing an electrical output signal when said feedback voltage exceeds a predetermined value;
    f. a secondary feedback voltage means controlling said integrator during reversed pressure conditions.

2. The apparatus of claim 1 wherein a filter means modifies the response of said comparator means to reject offset error and gradual deviations of said feedback voltage.

3. The apparatus of claim 1 wherein said diaphragm is secured in place by a means selected from the group consisting of adhesive bonding, welding and clamping.

4. The apparatus of claim 1 wherein said insulator is an insulating coating disposed upon and bonded to said electrodes.

5. The apparatus of claim 1 wherein said insulator is integral with said diaphragm.

6. The apparatus of claim 1 wherein said diaphragm is comprised of a plastic film with a metal coating on one face.

7. The apparatus of claim 1 wherein the active electronic devices implementing said conversion and amplifying means, said feedback means, and said comparator means are selected from the group consisting of transistors and digital microcircuits and linear microcircuits and mixed function microcircuits.

* * * * *